United States Patent
Damiano (10) Patent No.: US 10,307,068 B2
(45) Date of Patent: Jun. 4, 2019

(54) SYSTEMS AND METHODS FOR TIMING MEASUREMENTS IN A NON-INVASIVE BLOOD PRESSURE MEASUREMENT SYSTEM

(71) Applicant: DRÄGERWERK AG & CO. KGAA, Lübeck (DE)

(72) Inventor: Evan Damiano, Plymouth, MA (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 414 days.

(21) Appl. No.: 14/638,413

(22) Filed: Mar. 4, 2015

(65) Prior Publication Data
US 2015/0272454 A1 Oct. 1, 2015

Related U.S. Application Data (60) Provisional application No. 61/970,052, filed on Mar. 25, 2014.

(51) Int. Cl.
*A61B 5/00* (2006.01)
*A61B 5/022* (2006.01)
*A61B 5/0235* (2006.01)

(52) U.S. Cl.
CPC ........ *A61B 5/02225* (2013.01); *A61B 5/0235* (2013.01)

(58) Field of Classification Search
None
See application file for complete search history.

(56) References Cited

U.S. PATENT DOCUMENTS

| | | | | |
|---|---|---|---|---|
| 4,349,034 A | * | 9/1982 | Ramsey, III | A61B 5/02141 600/494 |
| 4,967,757 A | * | 11/1990 | Frankenreiter | A61B 5/022 600/495 |
| 5,224,484 A | | 7/1993 | Newell | |
| 5,240,008 A | | 8/1993 | Newell | |
| 5,285,791 A | | 2/1994 | Smith | |
| 5,337,751 A | | 8/1994 | Newell et al. | |
| 5,355,890 A | | 10/1994 | Aguirre et al. | |
| 5,993,396 A | * | 11/1999 | Friedman | A61B 5/02225 600/481 |
| 6,171,255 B1 | | 1/2001 | Ise et al. | |

(Continued)

FOREIGN PATENT DOCUMENTS

WO 2013/122608 8/2013

*Primary Examiner* — Navin Natnithithadha
*Assistant Examiner* — Sarah R Kingsley
(74) *Attorney, Agent, or Firm* — Wenderoth, Lind & Ponack, L.L.P.

(57) ABSTRACT

Disclosed are systems and methods for timing measurements in a non-invasive blood pressure measurement system. The systems and methods are capable of providing measurement results according to patient-specific time intervals. The disclosed systems may include a pump unit, signal acquisition circuit, user interface, clock, memory, microprocessor, power unit and communications module. The disclosed invention also contains a method for calculating an expected measurement duration. Additionally systems and methods for providing blood pressure results according to patient-specific time intervals using an expected measurement duration are discussed. Related apparatus, systems, methods and or/articles are described.

20 Claims, 5 Drawing Sheets

(56) References Cited

U.S. PATENT DOCUMENTS

| | | | | |
|---|---|---|---|---|
| 6,244,559 | B1 | 5/2001 | Hendriks | |
| 6,629,930 | B2* | 10/2003 | Palma | A61B 5/022 |
| | | | | 128/925 |
| 8,956,292 | B2* | 2/2015 | Wekell | G16H 15/00 |
| | | | | 600/301 |
| 2005/0101842 | A1* | 5/2005 | Suda | A61B 5/022 |
| | | | | 600/300 |
| 2005/0288571 | A1* | 12/2005 | Perkins | A61B 5/0002 |
| | | | | 600/407 |
| 2007/0038129 | A1* | 2/2007 | Kishimoto | A61B 5/022 |
| | | | | 600/485 |
| 2009/0054743 | A1* | 2/2009 | Stewart | G06T 11/206 |
| | | | | 600/301 |
| 2016/0174905 | A1* | 6/2016 | St. Pierre | A61B 5/022 |
| | | | | 600/301 |

* cited by examiner

SYSTEMS AND METHODS FOR TIMING MEASUREMENTS IN A NON-INVASIVE BLOOD PRESSURE MEASUREMENT SYSTEM

FIELD OF THE INVENTION

The present invention relates to a medical device used to improve the accuracy and timing of non-invasive blood pressure measurements.

BACKGROUND OF THE INVENTION

The consistent and continuous monitoring of health care vital signals such as blood pressure aids health care providers in diagnosing, monitoring and treating a patient. Many variants of automated methods for determining blood pressure measurements are known in the field. For example, International Publication No. WO 2013/122608 A1, U.S. Pat. No. 6,171,255B1, and U.S. Pat. No. 6,224,559B1 all discuss devices for noninvasive blood pressure measurements. These and all other referenced patents and applications are incorporated herein by reference in their entirety.

One form of a non-invasive blood pressure (NIBP) measuring method is an oscillometric method. In the oscillometric method changes in the sphygmomanometer cuff pressure corresponding to arterial flow resulting from the inflation or deflation of the cuff are measured using an electrical transducer. In the oscillometric method an inflatable cuff is inflated to a pressure above the estimated systolic pressure of a patient. The pressure in the cuff is then reduced slowly and steadily to below an estimated diastolic pressure. The oscillations detected by the transducer are monitored throughout the inflation and deflation processes. Mathematical algorithms are applied to the raw data to compute a systolic pressure, diastolic pressure and a mean arterial pressure. The process of determining these pressures automatically by inflating and deflating a sphygmomanometer cuff can be conducted by a blood pressure monitoring system. The time it takes to obtain a blood pressure measurement using an oscillometric method may vary from a few seconds to many minutes due to the uncertainty introduced by the NIBP cuff inflation and cuff deflation processes. For example, in a patient with a smaller upper arm circumference a NIBP cuff may not be properly aligned and slip during a measurement requiring multiple trials before an accurate measurement can be obtained. Additionally, the time needed for an accurate measurement may be impacted by the patient's movement or physiology. Typically, the time needed to acquire an accurate blood pressure measurement in an automated system, such as those referenced to above, may vary from 30 seconds to up to 3 minutes.

In the healthcare setting it is important for a clinician to be able to obtain a patient's blood pressure readings at pre-designated intervals. While the current technology allows clinicians to configure a non-invasive blood pressure (NIBP) time interval in a machine, this setting only guarantees when a blood pressure measurement will start. There is no guarantee that the device will be able to deliver the results according to the desired interval. As mentioned previously, it may take up to three minutes to obtain an accurate blood pressure measurement. For example, in the prior art, if a clinician specifies a 15 minute interval for blood pressure measurements, in actuality, a clinician may receive readings at: 12:01:00, 12:16:00, 12:32:05, 12:49:02, and so forth. However, a medical provider may actually have intended to have results for readings at more natural times such as: 12:00:00, 12:15:00, 12:30:00, 12:45:00, and 13:00:00. The ability to have readings at natural times may increase the ease of identifying and understanding trends in patient data, aid in the diagnosis and treatment of the patient and provide additional benefits in terms of hospital record keeping and billing procedures.

Therefore, it is desirable to have methods and systems for obtaining results from a non-invasive blood pressure measurement system at a patient-specific time interval indicated by a clinical professional.

SUMMARY OF THE INVENTION

The invention provides patient-specific methods and systems for obtaining results from a non-invasive blood pressure measurement system at times indicated by a clinical professional.

In an exemplary embodiment, the invention comprises a non-invasive blood pressure measurement system comprising a pump unit, signal acquisition circuit, user interface, clock, memory and microprocessor. The pump unit acquires a cuff pressure signal using an inflatable cuff and the signal acquisition circuit generates an oscillometric signal from the cuff pressure signal. The user interface allows a user to enter a patient-specific time interval. A memory stores the cuff pressure signal, the oscillometric signal, the patient-specific time interval, a buffer containing measurement durations and deviations, and an expected measurement duration. The microprocessor is operatively coupled to the pump unit, signal acquisition circuit, the user interface, the clock, and the memory. The microprocessor comprises at least one algorithm which uses cuff pressure signal and oscillometric signal to compute at least one blood pressure measurement. The microprocessor also comprises at least one algorithm which uses at least the clock, the buffer and the expected measurement duration to provide a result from at least one blood pressure measurement according to the patient-specific time interval. The at least one blood pressure measurement comprises at least one of a systolic pressure measurement, a diastolic pressure measurement and a mean arterial pressure measurement.

In another exemplary embodiment the invention comprises a method for calculating an expected measurement duration in an oscillometric blood pressure monitoring system comprising obtaining a first time from a clock, calculating at least one blood pressure measurement, obtaining a second time from a clock, calculating a measurement duration, obtaining from a memory the expected measurement duration, updating a memory, calculating a range of acceptable values, calculating a new expected measurement duration, and replacing the expected measurement duration stored in the memory with the new expected measurement duration.

In another exemplary embodiment, the invention comprises a method for obtaining measurements at patient-specific times in an oscillometric blood pressure monitoring system. The method further comprising receiving from a user a patient-specific time interval for obtaining measurements, obtaining an expected measurement time from a memory, and calculating a pre-start time, and sending a signal to start a non-invasive blood pressure (NIBP) measurement at said pre-start time.

In yet another exemplary embodiment, the invention comprises a patient monitoring system further comprising a patient monitor and a non-invasive blood pressure measurement system. The non-invasive blood pressure measurement system may comprise a pump unit, a signal acquisition circuit, and a microprocessor.

DETAILED DESCRIPTION OF THE INVENTION

It is an objective of the present invention to deliver non-invasive blood pressure measurements as closely as possible to times corresponding to an interval indicated by a clinical professional. As mentioned previously, a medical professional may require the results from an automated non-invasive blood pressure monitoring system at pre-determined intervals. These intervals may have clinical or administrative significance. While the prior art allows for obtaining automated blood pressure measurements, it does not guarantee that the measurements will be available for the clinician's use at the time intervals. The disclosed invention can be used as part of a hospital, nursing home, doctors office, home, or any combination thereof. For example, the invention's settings can be preconfigured by a physician at a medical care center and then the patient may be allowed to partake in normal daily activities before being removed from the blood pressure monitoring system.

Figure 1:
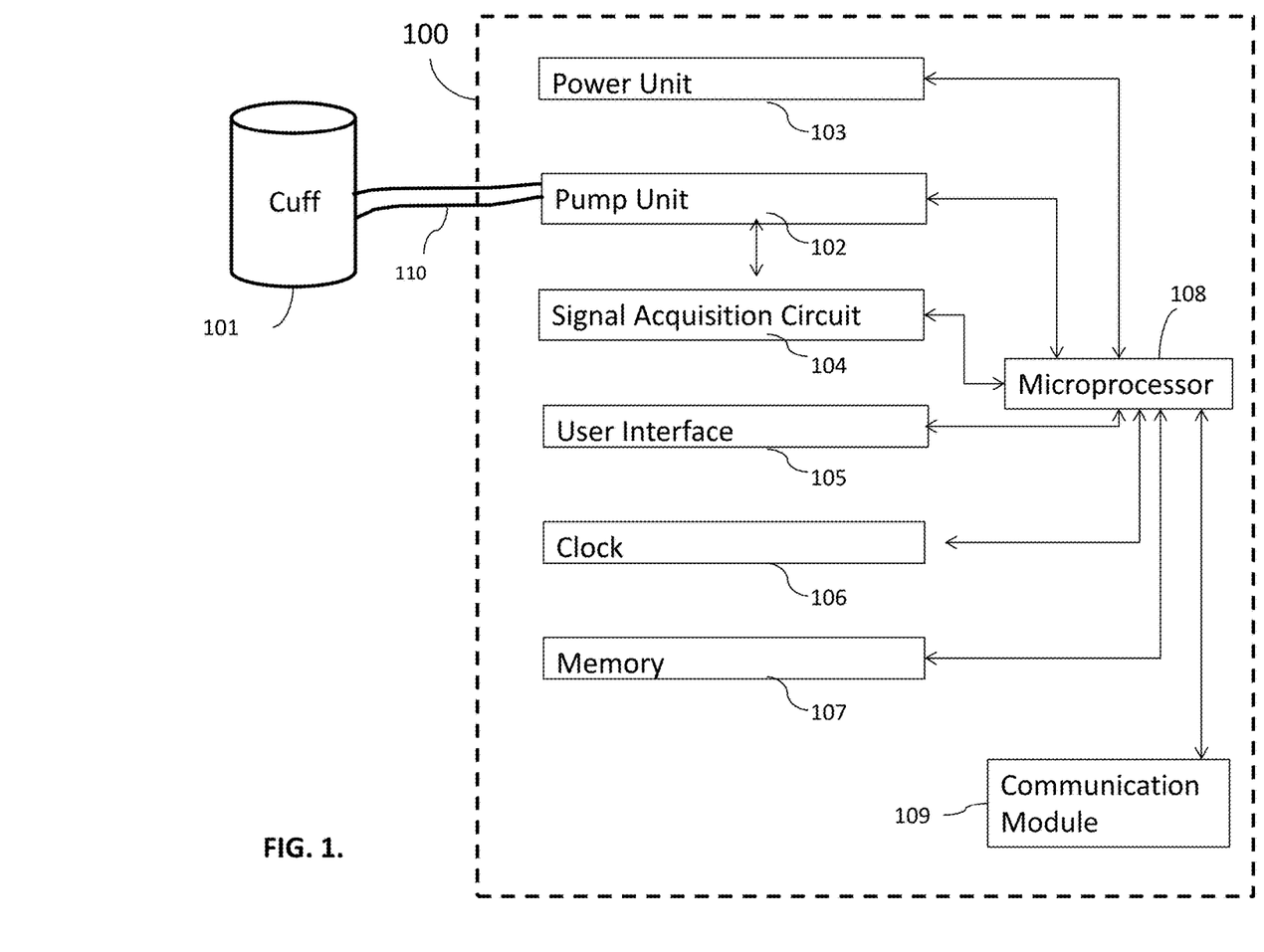
FIG. 1 is a block diagram of the components of the invention.

In FIG. 1 an embodiment of the system is provided. The disclosed system is a blood pressure monitoring system 100 comprising a pump unit 102, signal acquisition circuit 104, user interface 105, clock 106, memory 107 and microprocessor 108. The system may optionally include, for example, a communications module 109 and a power unit 103. The pump unit 102 is coupled via one or more air ducts and electrical connections 110 to a blood pressure cuff 101 and acquires a cuff pressure signal. The signal acquisition circuit 104 may perform signal processing techniques commonly known in the field in connection with a pressure transducer to compute an oscillometric signal from the cuff pressure signal. The pump unit 102 may comprise a pressure transducer, air pressure source, deflate valve(s), inflate valve(s), an exhaust and one or more air ducts. The pump unit is configured to be able to inflate and deflate a blood pressure cuff 101 in response to a command received from the microprocessor 108. The pump unit may also detect and transmit information regarding the cuff pressure to the signal acquisition unit 104 and the microprocessor 108. The pressure transducer in the pump unit 102 is used to sense pressure within the cuff 101. Signals received by the pressure transducer may be processed by the microprocessor 108 to produce blood pressure data. The microprocessor 108 may also transmit signals to inflate and deflate the blood pressure cuff 101 according to settings received by a user interface 105.

The system microprocessor 108 unit may utilize one or more algorithms stored in the system memory 107 to determine blood pressure measurements from the oscillometric signal. These algorithms may require as input the cuff pressure signal and/or the oscillometric signal. Blood pressure measurements derived from the oscillometric signal may include a systolic pressure, diastolic pressure and a mean arterial pressure.

Blood pressure measurements may be displayed on a user interface 105. The user interface 105 may include, for example, a monitor, a display, a keyboard, a mouse, a touchscreen, an interactive graphical user interface (GUI), keys, buttons, and the like. The user interface may, for example, also include stationary buttons the functions of which may vary according to what is displayed on a screen. Settings may be input into the user interface by, for example, a health care provider, a patient, or a technician. One such setting input by a user to the non-invasive blood pressure measurement system is a patient-specific time interval. As discussed previously, a clinician may, for example, prefer to receive blood pressure readings from a patient in natural intervals of fifteen minutes. The patient-specific time interval may be input in any time units including, without limit, minutes, seconds, hours or Julian time units. The microprocessor 108 may convert the patient-specific time interval into units compatible with those used by the system clock. The patient-specific desired time interval indicates the intervals at which the user requires consecutive blood pressure measurement results. The patient-specific time interval may be set according to the clinical needs of the patient or the administrative needs of the patient care facility. While a patient-specific time interval is discussed herein, in an alternative embodiment the user may enter a patient-specific time set comprised of discrete times at which the user may require NIBP measurements. Such a time set may be comprised of a set of times with unevenly spaced intervals. For example, a clinician studying the effects of a chemical compound may request NIBP measurements be taken every three minutes for the first fifteen minutes after exposure, then at the twentieth minute of exposure, the twenty-seventh minute of exposure, thirtieth minute of exposure and so forth. In such an example a clinician may wish to enter a time set of [12:00:00; 12:03:00; 12:06:00; 12:09:00; 12:12:00; 12:15:00; 12:20:00; 12:27:00, 12:30:00]. In an exemplary embodiment, the system may contain a display presenting the patient-specific time interval alongside patient data and information. The display may be integrated with the user interface and be interactive or touch-sensitive. The display may include a graphical user interface configured to receive and display the patient-specific time interval. A display may also be incorporated into a monitor.

In an embodiment of the system, the microprocessor 108 monitors the pressure in the cuff 101 by monitoring the pressure reading from a transducer contained within the pump unit 102. In order to calculate an oscillometric blood pressure measurement, the microprocessor 108 sends a signal to the pump 102 for the cuff 101 to be inflated to a target pressure, where the target pressure is a pressure estimated to be above the systolic blood pressure of the patient. The microprocessor monitors the pressure recorded by the transducer within the pump unit and the microprocessor sends a signal to the pump unit to begin the deflation of the cuff once the pressure transducer indicates that the target pressure is reached. The deflation of the cuff is slow and gradual such that one or more blood pressure measurements may be attained. The inflation of the cuff may be accompanied by the opening of one or more inflate valve(s) and the closing of one or more deflate valve(s). The deflation of the cuff may be accompanied by the opening of one or more deflate valve(s) and closing of one or more inflate valve(s). The signals to open and close the deflate and inflate valves may be sent by the microprocessor 108.

The signals sent by the microprocessor may be in response to executing algorithms stored in a memory component 107 of the device. The memory component 107 of the device may include the cuff pressure signal, the oscillometric signal, the patient-specific time interval, a buffer and an expected measurement duration. Information stored in the device's memory component may be organized into a buffer. The buffer may further comprise one or more measurement sets, wherein each measurement set comprises a measurement duration and a measurement deviation received and calculated from a NIBP measurement. The measurement duration is indicative of the time needed to obtain the NIBP measurement. The measurement deviation is indicative of the variation between the obtained measurement duration and those previously measured. For example, the measurement deviation may correspond to the standard deviation of the corresponding measurement duration from the expected measurement duration. Alternatively, the measurement deviation may be the absolute difference between a measured duration and the stored expected measurement duration. A measurement duration and measurement deviation may be considered corresponding if they belong to the same measurement set. The expected measurement duration stored in the memory 107 is calculated by at least one algorithm. The expected measurement duration may correspond, for example, to an average measurement duration, in which case, the algorithm calculates an arithmetic mean of one or more measurement durations stored in the system memory. In another embodiment the expected measurement duration may correspond to a weighted average, in which case, recent measurement durations may be given more weight than older measurement durations. In yet another embodiment, the expected measurement duration may correspond to a moving average in which only a subset of the last measurements are used in calculating an arithmetic mean. In another embodiment, the expected measurement duration may correspond to a combination of a moving average and a weighted average. In such an embodiment for example, the last three measurement durations may be given a weight, and the preceding three are given a second weight in calculating an expected measurement duration. In yet another embodiment, an algorithm may calculate the expected measurement duration such that it corresponds to a median value of the measurement durations stored in the memory. In an exemplary embodiment, algorithms used in the function of the device may be contained as software stored in a non-rewriteable machine-readable medium while information and data which may be edited can be contained in rewriteable machine-readable medium. These machine-readable medium may include, for example, magnetic discs, optical discs, memory, portable flash drives, flash storage, and the like.

The non-invasive blood pressure (NIBP) measurement system may also include a clock 106. The clock 106 provides accurate timing information to the microprocessor 108 and related components. In an exemplary embodiment of the system, the clock measures and provides time in Julian units. In an embodiment of the system, all times input by the user may be converted to units matching the internal clock. The internal clock of the device allows for accuracy in determining the elapsed measurement duration. For example, in a hospital setting two wall clocks in separate rooms may not display the same exact time. If a patient is transported from one room to another during the process of automated blood pressure monitoring, a clinician may inaccurately measure the time elapsed and measurement duration. In contrast, the internal clock of the blood pressure monitoring system provides a reliable and consistent measure of time.

The blood pressure monitoring system may also include a power unit 103. The power unit may comprise, for example, a battery and a power coupler. The power coupler may be configured, for example, to receive power from a docking station to which this blood pressure monitoring system may attach to. The power coupler may also be configured, for example, to receive power directly from a AC wall unit. The battery in the power unit 103 may be non-rechargeable or a rechargeable unit which is recharged from the power coupler. Examples of rechargeable units include a NiCad battery, a LiPo battery, a NiMH battery or the like.

An exemplary embodiment of the system may also include a communications module 109. A communications module 109 may contain electro-mechanical parts used by the microprocessor 108 to transmit patient data and information, blood pressure measurements and settings to a remote database. For example, the system may be configured to transmit hourly blood pressure readings to the patient's electronic medical file for review by a physician. The communications module 109 may allow for wired and wireless communication. In a wired configuration, for example, the blood pressure monitoring system may be connected via Ethernet to a hospital network. In a wireless configuration the blood pressure monitoring system may broadcast using wireless technologies which may include at least one of Wireless Local Area Network (WLAN), Wireless Patient Area Network (WPAN) or Wireless Wide Area Network (WWAN). In an exemplary embodiment the communications module 109 may be configured to automatically transmit information acquired by the blood pressure monitoring system wirelessly while the monitoring system is mobile.

The blood pressure monitoring system may be stationary and associated with a specific hospital bed. The blood pressure monitoring system may also be ambulatory and move with the patient throughout the hospital transmitting the acquired patient data and information. The blood pressure monitoring system may also be integrated into a patient monitoring device. In such a scenario, the patient monitoring device includes a non-invasive blood pressure measurement device and is capable of receiving a patient-specific time interval, obtaining an expected measurement duration, calculating a pre-start time and sending a signal to start a non-invasive blood pressure measurement at said pre-start time. The patient monitoring device may be portable and able to dock to a docking station from which it receives power and/or patient and system data and information. The patient monitoring device may also be stationary. In such configurations, the patient monitoring device may transmit patient data and information to a central monitoring station, which may monitor patient data and information from a number of patients. The patient monitoring device may contain a processor capable of executing an algorithm to calculate an expected measurement duration and an algorithm to obtain measurements at patient-specific times. The patient monitoring device may, for example, also contain a display, capable of displaying patient data and information including the NIBP measurements results received from a blood pressure measurement device and the patient-specific time interval. The patient monitoring device may be attached to one or more medical devices each capable of receiving one or more signals from the patient corresponding to the physiological state of the patient. For example, a patient monitoring device may be connected to an electrocardiogram and a non-invasive blood pressure measurement device and be configured to receive blood pressure measurements according to a time interval input by a nurse into a touch-screen monitor.

In an embodiment, a patient monitoring system may comprise a patient monitor and a non-invasive blood pressure measurement system. The patient monitor may be capable of receiving and displaying physiological parameters from a patient. The non-invasive blood pressure measurement system may be comprised of a pump unit capable of acquiring a cuff pressure signal using an inflatable cuff, a signal acquisition circuit capable of generating an oscillometric signal from the cuff pressure signal, and a microprocessor which is operatively coupled to the pump unit and the signal acquisition circuit. As will be discussed further below, the microprocessor may be capable of computing a blood pressure measurement from the oscillometric signal at a patient-specific time interval based on an expected measurement duration. These calculations and computations may be performed by the microprocessor by executing algorithms stored on a memory component.

Figure 2:
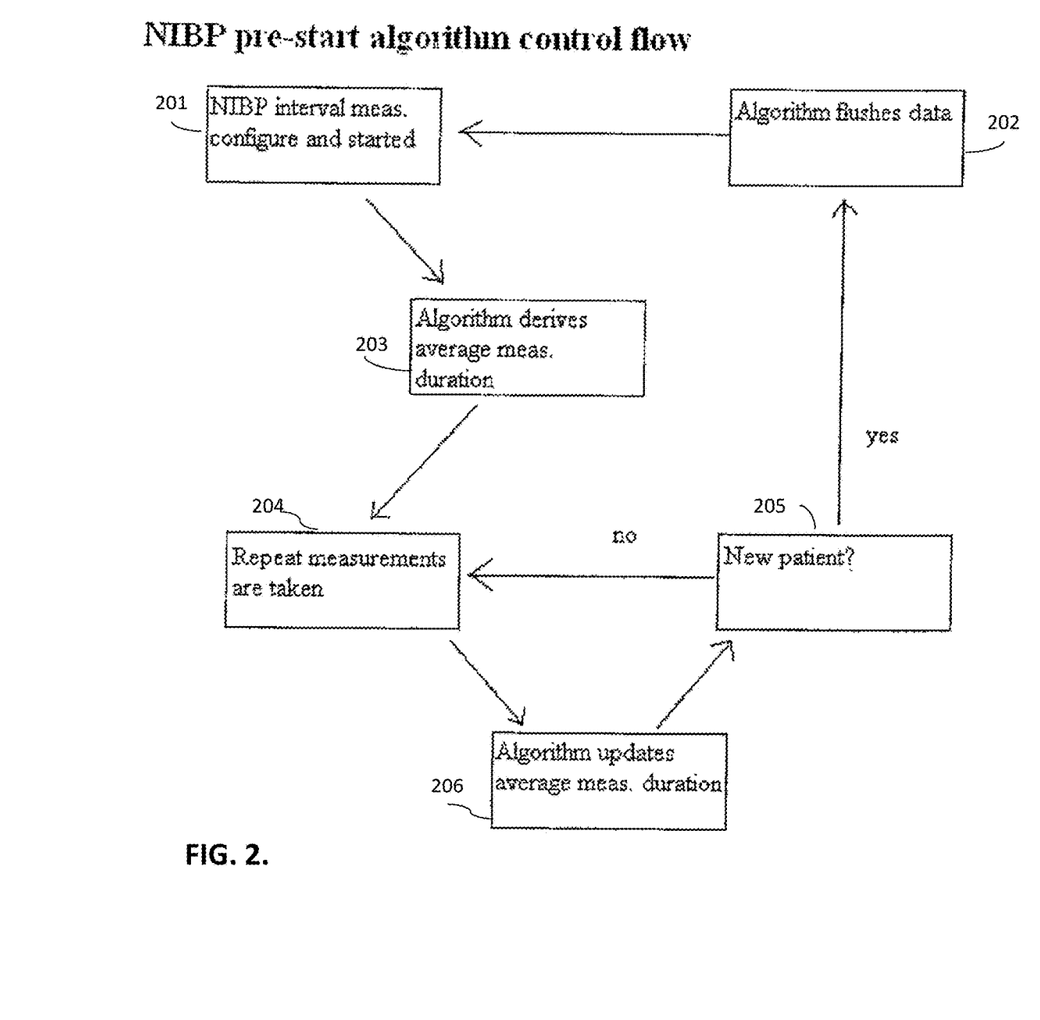
FIG. 2 is a flowchart of a non-invasive blood pressure (NIBP) pre-start algorithm control flow.

FIG. 2 is a flowchart demonstrating the interactions between methods used to calculate an expected measurement duration and a pre-start time in a system for timing NIBP measurements. In an exemplary embodiment of the system, the system first assesses if the patient is a new patient 205, if so, the algorithm flushes the data or deletes entries in the buffer stored in the memory 202. The contents of the buffer may also be cleared in response to a power cycle. The method then receives information regarding the patient-specific time interval 201. The method implements an algorithm which calculates an expected measurement duration which in this example, corresponds to an arithmetic average measurement duration 203. Successive measurement durations are taken 204 and the method updates the expected measurement duration 206. If the patient is not a new patient (and the system has information regarding the patient's previous measurements already stored in the memory), the algorithm starts by taking successive measurement durations 204.

Disclosed is a method for calculating an expected measurement duration 206 executed by the microprocessor 108. A flowchart of an algorithm for obtaining an expected measurement duration in an oscillometric blood pressure monitoring system is provided in FIG. 3. The algorithm executed by the microprocessor 108 would first obtain a first time in step 301 from the system clock 106. Then the algorithm would calculate at least one blood pressure measurement in step 302. The algorithm may comprise computer-readable instructions stored by a memory 107 and executed by the microprocessor 108. The instructions to calculate a blood pressure measurement may include instructions for the microprocessor 108 to signal the pump unit 102 to adjust the air flow. As explained above, a NIBP measurement using the oscillometric method may include, for example, at least one of a systolic pressure, diastolic pressure and a mean arterial pressure. In a third step 303, the method obtains a second time from the system clock. In an embodiment of the method the times provided by the system clock are in Julian units. The algorithm then computes the measurement duration in step 304 which is indicative of the time necessary for the NIBP system to obtain at least one blood pressure measurement. This measurement duration is calculated based on the difference between the first and second times received from the system clock. The method then obtains from the memory the stored expected measurement duration in step 305.

Figure 3:
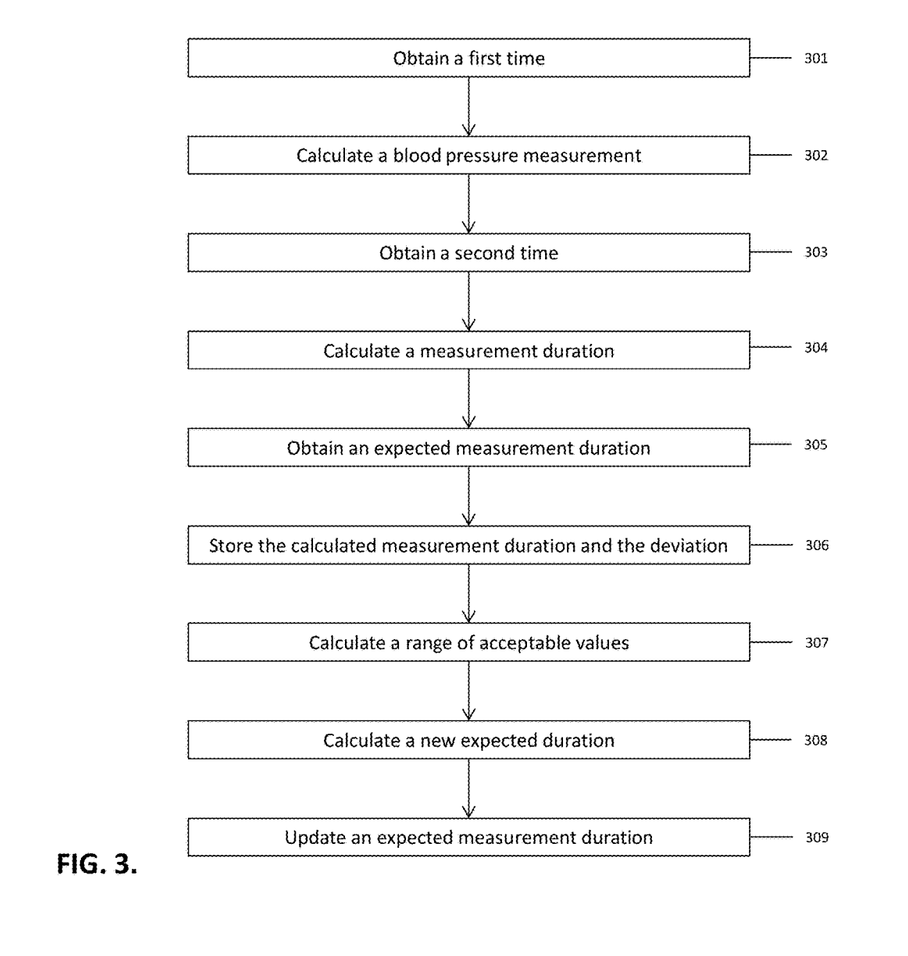
FIG. 3 is a flowchart of a method for calculating an expected measurement duration in an oscillometric blood pressure monitoring system.

The method then updates the memory with the measurement duration and a deviation in step 306. In an exemplary embodiment, the measurement duration and deviation may be organized in a buffer in the memory. The deviation value input into the buffer is indicative of the variation of the currently obtained measurement duration from past measurement durations. In one embodiment, for example, the deviation is equivalent to the absolute difference between the currently obtained measurement duration and an expected measurement duration stored in the memory. In another embodiment, for example, the deviation may be equivalent to the standard deviation of the current obtained measurement duration with respect to an expected measurement duration stored in the memory.

After updating the buffer with information from the current measurement, the method calculates from the buffer a range of acceptable values in step 307. This range of acceptable values corresponds to a range which will determine whether a measurement duration be included in a calculation for the new expected measurement duration in step 308. The range of acceptable values corrects for instances in which multiple trials may be necessary before being able to obtain an accurate blood pressure measurement. For example, in the case of a child who interrupts the blood pressure measurement a number of times, a machine or clinician may have attempted three trials prior to being able to attain a blood pressure measurement. In this example, the measurement duration may be extremely large, for example, 5 minutes. This value is not indicative of the expected measurement duration. The example measurement duration of 5 minutes is an outlier, and calculating a buffer with a range of acceptable values, prevents the outlier from impacting the calculation of an expected measurement duration. The expected measurement duration is updated in the memory in step 309 and used to determine the pre-start time.

In an embodiment of the system, the range of acceptable values calculated in step 307 may be set at two standard deviations above and below the previously calculated expected measurement duration. In such an exemplary embodiment, the standard deviation values may be calculated from the entire set of measurement durations available in the buffer. The expected measurement duration may be calculated solely based on the measurement durations contained within the range of acceptable values, as discussed below. In an embodiment of the system, the range of acceptable values may be set to be tolerant of a high spread of measurement durations for initial measurements and the range may be adjusted to be less tolerant as the patient has multiple blood pressure measurements.

In an embodiment of the system, the buffer stored in the memory may be of limited size or hold a buffer capacity. For example, the buffer may be limited to the last ten or twenty measurement sets and their corresponding measurement durations and deviations. In such an embodiment, if the algorithm being executed by the microprocessor determines that the addition of a new measurement set to the buffer would exceed the buffer capacity, in other words if the current buffer size exceeds a buffer size limit or buffer capacity, the oldest measurement set from the buffer may be deleted prior to the new measurement set being added to the buffer.

After calculating a range of acceptable values from the values stored in the buffer, the method calculates a new expected measurement duration in step 308. In an embodiment of the method, the new expected measurement duration is the arithmetic mean of measurement durations for all measurement sets with measurement durations which fall within the previously determined range of acceptable values. The memory is updated to contain the new expected measurement duration. In an embodiment of the system, the new expected measurement duration is also used to update the deviation parameter included in the measurement sets stored in the buffer memory in step 309.

Figure 4:
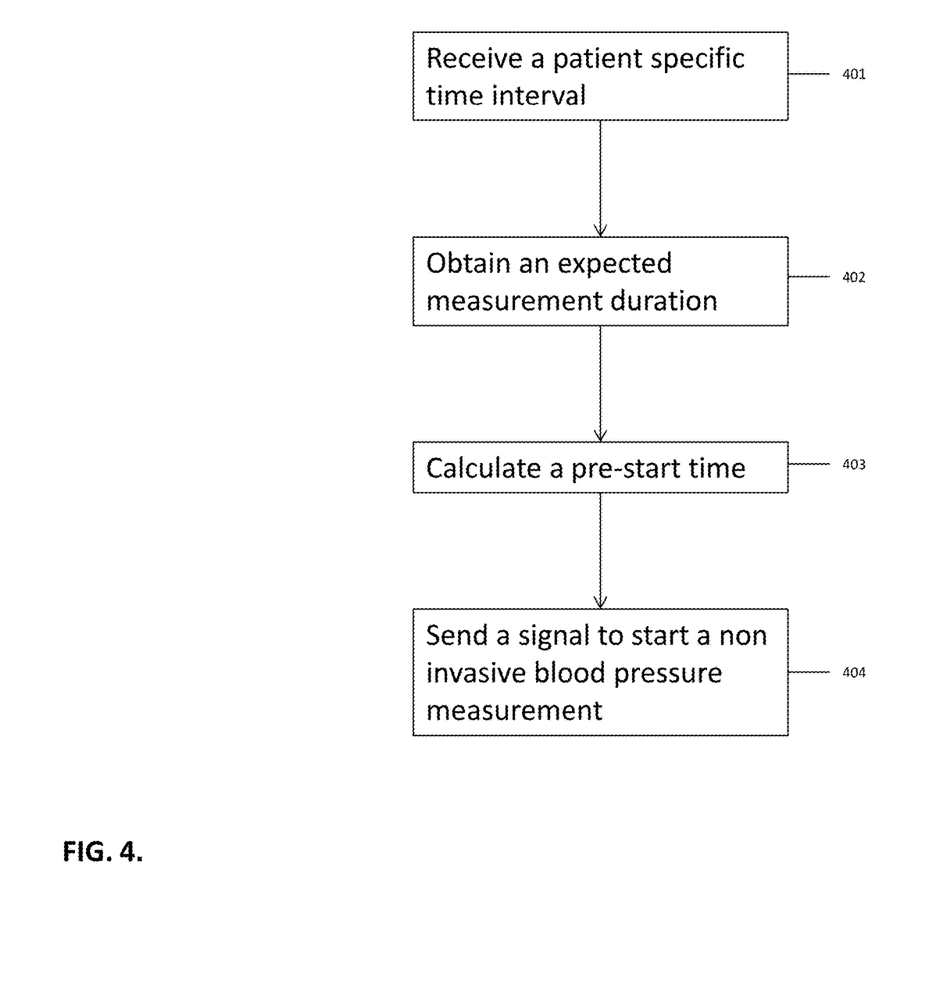
FIG. 4 is a flowchart of a method for obtaining measurements at patient-specific times in an oscillometric blood pressure monitoring system.

FIG. 4 demonstrates a method for obtaining measurements at patient-specific times in an oscillometric blood pressure monitoring system. The method first receives from a user a patient-specific time interval for obtaining measurement results in step 401. As disclosed previously, patient-specific time intervals may be received via a user interface 105. The value of the patient-specific time interval is stored in the memory 107 of the device. The algorithm being executed by the microprocessor 108 then obtains an expected measurement duration in step 402 from the memory 107.

The method then calculates a pre-start time in step 403. The pre-start time may correspond to the difference between a time indicated by the patient-specific time interval and the expected measurement duration. For example, if a physician indicates a patient-specific time interval of ten minutes from 12 pm a time indicated by the patient-specific time interval is 12:10:00. If the stored expected measurement duration is 00:01:05, the pre-start time is calculated to be, for example, 12:08:55. In an alternative embodiment in which the user has entered a discrete time set, the processor may compute the patient-specific interval for each value in the discrete time set and then calculate the pre-start time. Alternatively, for example, the pre-start time may be computed by the processor directly, by subtracting the expected measurement duration from the time indicated by the entered discrete time set. Lastly, the microprocessor 108 sends a signal to the pump unit 102 to start a non-invasive blood pressure measurement (NIBP) at the calculated pre-start time in step 404.

The calculated pre-start time encompasses the patient-specific adjustment for physiological, equipment-based, and other considerations which comprise the expected duration of a non-invasive blood pressure measurement. This proprietary calculation, available in the patient monitoring device's memory may then be passed to other network systems as a patient-specific parameter when monitoring of the patient is transferred to another bedside monitor via the network or in the case of physical transfer.

Figure 5:
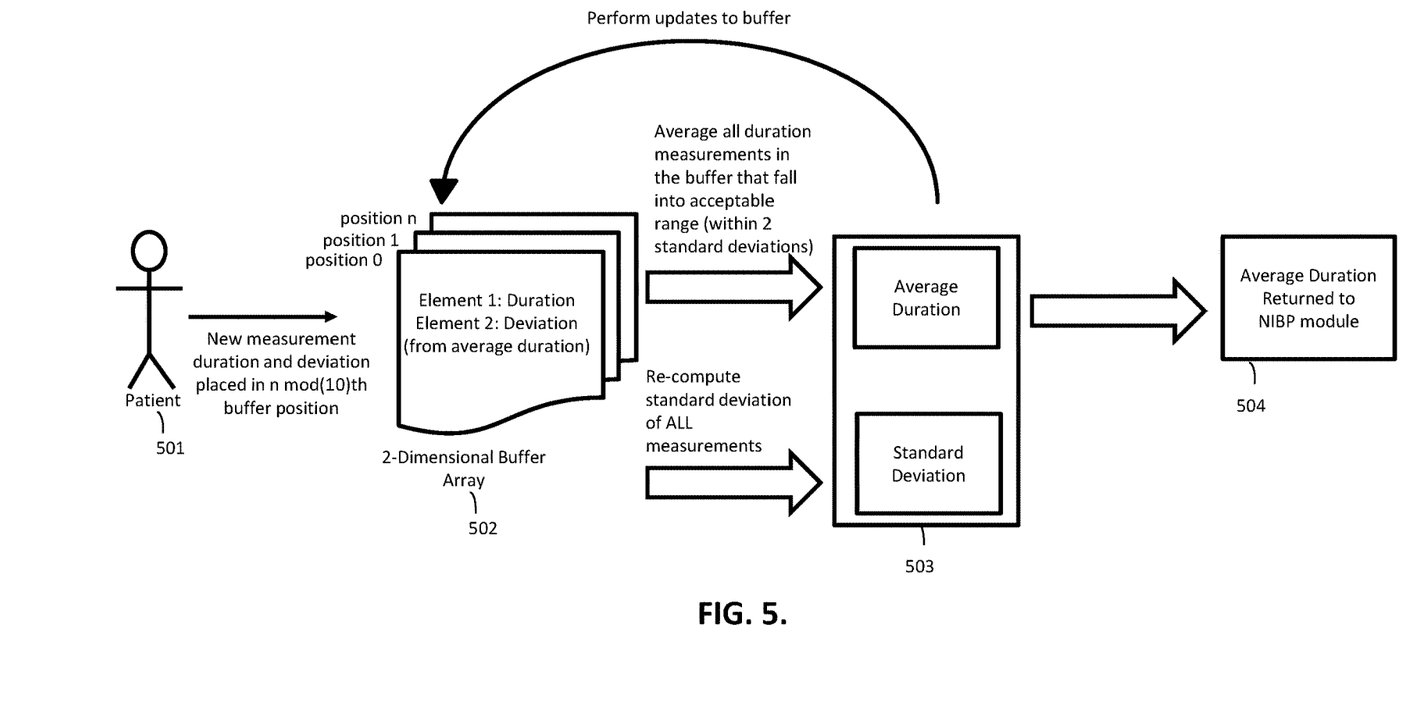
FIG. 5 is a diagram depicting an embodiment of the systems and methods described herein.

An exemplary embodiment of the above described non-invasive blood pressure measurement system capable of obtaining measurements at patient-specific times according to an expected measurement duration is illustrated in FIG. 5. As shown in FIG. 5, a non-invasive blood pressure measurement is obtained from a patient 501 and stored in an organized buffer 502 within the memory of the system. The shown buffer 502 has a buffer size of 10 and stores the measurement duration and deviation. In this embodiment, the expected measurement duration corresponds to the average duration. Additionally, the deviation value is, for example, an absolute difference from the average duration. In this exemplary embodiment, the acceptable range of values is set to two standard deviations. Additionally the deviation is set to be computed from all the measurements stored within the buffer. The average duration and standard deviation are computed accordingly 503. Additionally, the values stored in the buffer 502 are updated accordingly. In this example, the average duration (which corresponds to the expected measurement duration) is passed to a NIBP module 504.

Every blood pressure measurement obtained by the system leads to an update of the buffer and may correspond to changes in the expected measurement duration. In doing so the system is able to provide blood pressure results at times close to the patient specific time interval despite changes to a trend in a the patient's blood pressure measurement duration. The disclosed system is also able to prevent unnecessary changes in the pre-start time by having a method for calculating an expected measurement duration which controls for outliers. Various aspects of the subject matter described herein may be realized in electromechanical components such as integrated circuitry, specialized circuitry, computer hardware, firmware, software and/or a combination thereof. Implementations of the disclosed system may include computer programs which are executable or implementable on at least one programmable processor (special or general purpose). The processor may be coupled to one or more memory components, interfaces for receiving and transmitting data and instructions, an input device and an output device.

The software components may include machine readable instructions for a programmable processor and be implemented in high-level procedural language, and/or object oriented programming language, and/or assembly/machine language.

Although exemplary embodiments of the present invention have been described above, it is not limited thereto. The appended claims should be construed broadly to include other variants and embodiments of the invention which may be made by those skilled in the art without departing from the scope and range of equivalents of the invention. This disclosure is intended to cover any adaptations or variations of the embodiments discussed herein.

The invention claimed is:

1. A non-invasive blood pressure measurement system comprising:
   a pump unit comprising at least one of a pressure transducer, an air pressure source, at least one air duct, at least one deflate valve, at least one inflate valve, or an exhaust, the pump unit configured to acquire a cuff pressure signal using an inflatable cuff coupled thereto;
   a signal acquisition circuit configured to generate an oscillometric signal from the cuff pressure signal; and
   a microprocessor operatively coupled to the pump unit and the signal acquisition circuit;
   wherein the microprocessor:
      receives a patient-specific time interval for obtaining measurement results based on a desired time interval input into a user interface;
      obtains an expected measurement duration based on an arithmetic average value of a plurality of previous measurement durations;
      calculates a pre-start time corresponding to a difference between the desired time interval indicated by the patient-specific time interval and the expected measurement duration; and
      sends a signal at the pre-start time to inflate or deflate the inflatable cuff to start a non-invasive blood pressure (NIBP) measurement using the pump unit and the signal acquisition circuit;
   wherein:
   the patient-specific time interval comprises a desired time difference between consecutive blood pressure measurements;

the expected measurement duration comprises an expected amount of time required to obtain the NIBP measurement; and the inflatable cuff inflates or deflates based on the signal.

2. The system of claim 1, further comprising memory configured to store the cuff pressure signal, the oscillometric signal, the patient-specific time interval, and the expected measurement duration, wherein the memory is operatively coupled to the microprocessor.

3. The system of claim 2, further comprising the microprocessor calculating the expected measurement duration based on information from the memory.

4. The system of claim 1, further comprising a clock configured to measure and provide a time, wherein the clock is operatively coupled to the microprocessor.

5. The system of claim 1, wherein the cuff pressure signal and the oscillometric signal are obtained using a non-invasive blood pressure (NIBP) measurement method.

6. The system of claim 1, further comprising the user interface capable of receiving the patient-specific time interval.

7. The system of claim 1, wherein the microprocessor is configured to convert the patient-specific time interval into a unit of time corresponding to that used by a clock.

8. The system of claim 1, further comprising a communication module comprising an Ethernet connection, a Wireless Local Area Network connection, or a Wireless Wide Area Network connection, the communication module configured to receive and transmit wireless signals and wired signals.

9. The system of claim 2, further comprising a communication module configured to transmit information stored in the memory to a remote database and a monitoring station.

10. The system of claim 1, wherein the system is a stationary blood pressure monitoring system.

11. The system of claim 1, wherein the system is an ambulatory blood pressure monitoring system.

12. The system of claim 1, wherein a blood pressure measurement comprises at least one of a systolic pressure, a diastolic pressure and a mean arterial blood pressure.

13. The system of claim 1, further comprising a power unit configured to provide power to the system using at least one of a battery and a connection to a wall AC unit.

14. A patient monitoring system comprising:
a patient monitor capable of receiving and displaying physiological parameters; and
a non-invasive blood pressure measurement system comprising:
a pump unit comprising at least one of a pressure transducer, an air pressure source, at least one air duct, at least one deflate valve, at least one inflate valve, or an exhaust, the pump unit configured to acquire a cuff pressure signal using an inflatable cuff coupled thereto;
a signal acquisition circuit configured to generate an oscillometric signal from the cuff pressure signal; and
a microprocessor operatively coupled to the pump unit and the signal acquisition circuit;
wherein the microprocessor:
receives a patient-specific time interval for obtaining measurement results based on a desired time interval input into a user interface;
obtains an expected measurement duration based on an arithmetic average value of a plurality of previous measurement durations;
calculates a pre-start time corresponding to a difference between the desired time interval indicated by the patient-specific time interval and the expected measurement duration; and
sends a signal at the pre-start time to inflate or deflate the inflatable cuff to start a non-invasive blood pressure (NIBP) measurement using the pump unit and the signal acquisition circuit at the pre start time;
wherein:
the patient-specific time interval comprises a desired time difference between consecutive blood pressure measurements;
the expected measurement duration comprises an expected amount of time required to obtain the NIBP measurement; and the inflatable cuff inflates or deflates based on the signal.

15. The system of claim 14, wherein the non-invasive blood pressure measurement system further comprises memory operatively coupled to the microprocessor and configured to store the cuff pressure signal, the oscillometric signal, the patient-specific time interval, and the expected measurement duration.

16. The system of claim 15, wherein the microprocessor calculates the expected measurement duration based on information from the memory.

17. The system of claim 15, further comprising a communication module comprising an Ethernet connection, a Wireless Local Area Network connection, or a Wireless Wide Area Network connection, the communication module configured to transmit information stored in the memory to a remote database and a monitoring station.

18. A system for obtaining measurements at patient-specific times in an oscillometric blood pressure monitoring system, comprising:
means for receiving a patient-specific time interval for obtaining measurement results from a user via a user interface;
means for obtaining an expected measurement duration based on an arithmetic average value of a plurality of previous measurement durations;
means for calculating a pre-start time corresponding to a difference between the desired time interval indicated by the patient-specific time interval and the expected measurement duration; and
means for sending a signal at the pre-start time to inflate or deflate an inflatable cuff to start a non-invasive blood pressure (NIBP) measurement;
wherein:
the patient-specific time interval comprises a desired time difference between consecutive blood pressure measurements;
the expected measurement duration comprises an expected amount of time required to obtain the NIBP measurement; and
the inflatable cuff inflates or deflates based on the signal.

19. The system of claim 1, wherein each of the plurality of previous measurement durations falls within a predefined acceptable range of values.

20. A non-invasive blood pressure measurement system comprising:
a pump unit comprising at least one of a pressure transducer, an air pressure source, at least one air duct, at least one deflate valve, at least one inflate valve, or an exhaust, the pump unit configured to acquire a cuff pressure signal using an inflatable cuff coupled thereto;

a signal acquisition circuit configured to generate an oscillometric signal from the cuff pressure signal; and a microprocessor operatively coupled to the pump unit and the signal acquisition circuit;

wherein the microprocessor:

receives a patient-specific time interval for obtaining measurement results based on a desired time interval input into a user interface;

obtains an expected measurement duration based on an arithmetic average value of a plurality of previous measurement durations;

calculates a pre-start time for sending a signal to inflate or deflate the inflatable cuff to start a non-invasive blood pressure (NIBP) measurement using the pump unit, the pre-start time being determined by subtracting the expected measurement duration from a time obtained by adding the desired time interval indicated by the patient specific time interval to a time when the cuff pressure signal is last acquired during an immediately preceding NIBP measurement using the pump unit;

sends the signal at the pre-start time to inflate or deflate the inflatable cuff to start the NIBP measurement using the pump unit and the signal acquisition circuit;

wherein:

the patient-specific time interval comprises a desired time difference between consecutive blood pressure measurements;

the expected measurement duration comprises an expected amount of time required to obtain the NIBP measurement; and the inflatable cuff inflates or deflates based on the signal.

* * * * *